United States Patent [19]

Bechtle

[11] Patent Number: 4,531,944

[45] Date of Patent: Jul. 30, 1985

[54] EYE DROP APPLICATION AID

[76] Inventor: Samuel J. Bechtle, 24821 Argus, Mission Viejo, Calif. 92692

[21] Appl. No.: 489,691

[22] Filed: Apr. 28, 1983

[51] Int. Cl.³ .............................................. A61M 1/00
[52] U.S. Cl. .................................................... 604/302
[58] Field of Search ................................ 604/300–302

[56] References Cited

U.S. PATENT DOCUMENTS

| | | |
|---|---|---|
| 2,482,431 | 9/1949 | Okawa . |
| 2,516,818 | 7/1950 | West . |
| 2,589,178 | 3/1952 | Wintle, Jr. . |
| 3,016,898 | 1/1962 | Erwin . |
| 3,058,466 | 10/1962 | Routsong . |
| 3,279,466 | 10/1966 | Mings . |
| 3,446,209 | 5/1969 | Macha . |
| 3,779,245 | 12/1973 | Windsor ............................. 604/300 |
| 3,888,251 | 6/1975 | Harrison . |
| 3,934,590 | 1/1976 | Campagna et al. . |
| 3,945,381 | 3/1976 | Silver . |
| 4,002,168 | 1/1977 | Petterson . |

FOREIGN PATENT DOCUMENTS 1259476  3/1961  France ............................. 604/302

*Primary Examiner*—Stephen C. Pellegrino
*Attorney, Agent, or Firm*—John A. Waters

[57] ABSTRACT

An eye drop application aid for self-application of droplets of ophthalmic solution by an individual includes a housing having a top, side walls and an open bottom, with the lower periphery of the side walls being contoured to conform to the facial area surrounding the eye socket. The housing top includes an eye drop dispenser seat with a central droplet discharge aperture therethrough for receiving and supporting the dispensing end of an eye drop dispenser. A vertical alignment indicator is mounted on the housing in view of the eye being treated to achieve vertical alignment of the eye drop dispenser end before dispensing droplets of ophthalmic solution to insure accurate application of the droplets to the eye. An eye distracting orifice in the housing top in view of the eye being treated focuses the eye's attention on the orifice instead of the dispenser end to avoid premature blinking before the droplet has contacted the eye. Removeably mounted dispenser seats are utilized to permit interchangeability of differently configured dispenser seats to accommodate dispensers of differing configurations.

8 Claims, 8 Drawing Figures 4,531,944

EYE DROP APPLICATION AID

BACKGROUND OF THE INVENTION

1. Field of The Invention

The present invention relates to the application of eye drops, and, more particularly, to an eye drop application aid for self-application of droplets of opthalmic solution by an individual.

2. Description of The Prior Art

The use of eye drops for the care and treatment of the eyes is widespread. A wide variety of opthalmic solutions, prescription and non-prescription, are designed to be applied to the eyes in droplet form to alleviate conditions ranging from simple eye strain to various eye diseases such as glaucoma. Generally, eye drops are supplied to the user either in a bottle with a conventional medicine dropper type of cap or in a soft-sided squeeze bottle having a nozzle with a discharge opening. The opthalmic solution is introduced into the eye by holding the end of the medicine dropper or the bottle nozzle over the eye and squeezing the medicine dropper bulb or squeeze bottle sides to discharge droplets of the solution. Typically, the eye drops are self-administered, which not only presents a challenge but which invariably results in one or more problems. This is especially true in the case of the infirmed and the elderly, particularly when they live alone and have no choice but to self-administer the eye drops. Improper application can negate the desired effects of the opthalmic solution, as well as waste large amounts of the solution which can be costly in the case of expensive prescription solutions. There is also the serious danger of accidental physical contact of the bottle nozzle or medicine dropper end with the eye which can produce serious eye injury.

Because of the frequent problems with self-administration of eye drops, a wide variety of devices have been developed over the years to facilitate the self-administration of eye drops. Structures ranging from complex dispensers to a variety of dispenser alignment supports have been proposed with varying degrees of success. However, to date, none has been entirely satisfactory. Many of the devices are expensive and difficult to use, especially by the elderly. On the other hand, the less costly and more simplified devices have not resulted in consistent accuracy of the eye drop application to warrant their use. While many of the prior art devices successfully position the dispenser a predetermined distance from the eye, they do not accomplish precise vertical alignment, which more often than not results in a skewed application of the droplets, thus failing to yield the desired uniform coating of the eye surface.

Another problem with virtually all of the prior art devices is that they result in the user staring at the dispenser end and the impending droplet, too often resulting in blinking of the eye before the droplet has contacted the eye's surface, leading to a totally unsuccessful application attempt.

Yet another problem with most of the prior art devices is that they are customized to be useable only with a particular type and size of dispenser and thus have no versatility for use with a variety of dispensers.

Accordingly, an eye dropper application aid which would eliminate the problems of the prior art devices would be welcomed by all who are faced with self-administering eye drops, especially the infirmed and the elderly and those who must self-administer eye drops on a regular and frequent basis.

SUMMARY OF THE INVENTION

According to the present invention, there is provided an eye dropper application aid for self-application of droplets of opthalmic solution by an individual which is simple and inexpensive in construction and which is easy to use with consistent accuracy and successful droplet applications. The application aid can be used with a variety of dispenser configurations.

The unique eye drop application aid comprises a housing having a top, side walls and an open bottom, with the lower periphery of the side walls being contoured to conform to the facial area surrounding the eye socket. An eye drop dispenser seat in the housing top has a central droplet discharge aperture therethrough and receives and supports the dispensing end of an eye drop dispenser a predetermined distance directly above the center of the eye and permits droplets of opthalmic solution to be applied to the eye. In the preferred embodiment, the dispenser seat is removeably mounted in the housing top to permit interchangeability of differently configured dispenser seats to accommodate dispensers of differing configurations.

The preferred embodiment also includes an alignment indicator means mounted to the housing adjacent to the dispenser seat in view of the eye being treated to permit vertical alignment of the eye drop dispenser end by head movement before dispensing droplets of the opthalmic solution to insure accurate application of the droplets to the eye. The preferred embodiment further includes an eye distracting orifice in the housing top adjacent to the dispenser seat in view of the eye being treated which permits light to pass therethrough to focus the eye's attention on the orifice, instead of the dispenser end and the impending droplet of opthalmic solution, to avoid premature blinking before the droplet has contacted the eye.

The vertical alignment indicator which is especially preferred comprises an indicator element freely rotatably mounted parallel to the housing side wall, preferably interior of the housing on an axle pin which is perpendicularly mounted to the housing side wall. The indicator element has an indicator point at one end and a center of gravity nearer the other end below the point of rotatable mounting. The indicator point, which preferably is perpendicular to the main body of the indicator element and extends toward the dispenser seat, passes by the eye distracting orifice during rotation between the eye and the orifice. The force of gravity causes the indicator element to constantly seek a vertical orientation. Accordingly, when the indicator point is positioned at the orifice, the eye drop dispenser end will be vertically aligned above the eye to be treated.

DESCRIPTION OF THE PREFERRED EMBODIMENTS

Figure 1:
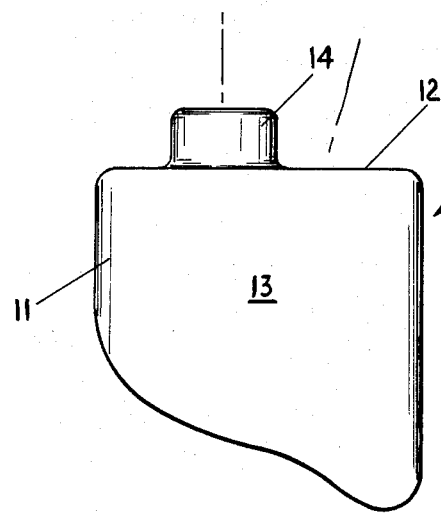
FIG. 1 is a side elevational view of the eye drop application aid of the present invention.
Figure 2:
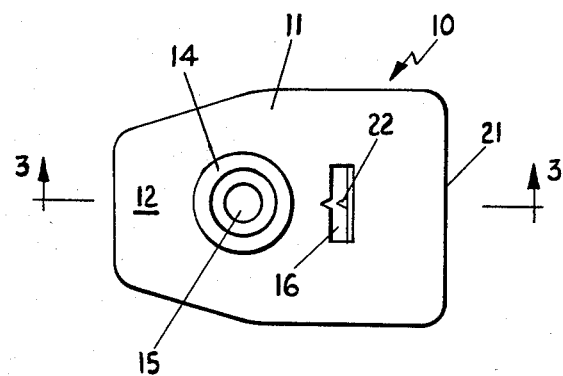
FIG. 2 is a plan view of the application aid of FIG. 1.
Figure 3:
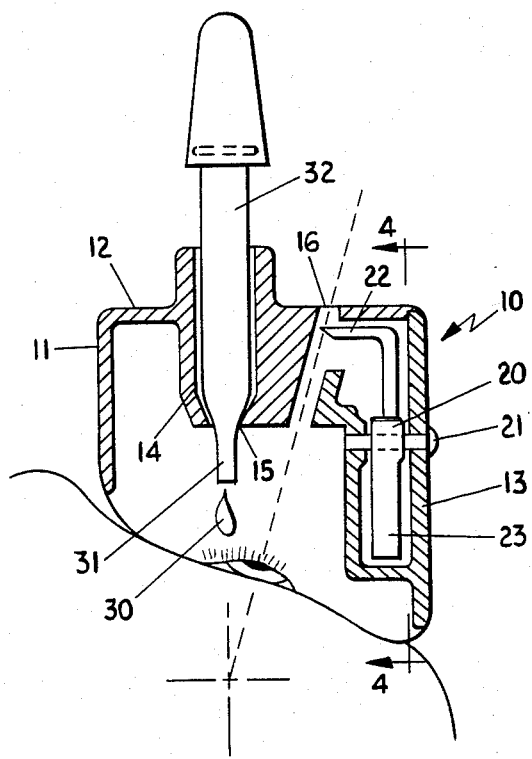
FIG. 3 is a side cross-sectional view of the application aid taken along the line 3—3 of FIG. 2 and shown in use in applying a droplet of opthalmic solution to the user's eye.

Referring to the drawings in greater detail, FIGS. 1-4 illustrate a preferred embodiment of eye drop application aid 10. As shown, application aid 10 includes a housing 11 having top 12, side walls 13 and an open bottom. The lower periphery of side walls 13 are contoured to conform to the facial area surrounding the eye socket, i.e., the nose, the cheek and the lower forehead, as shown in FIG. 3. Application aid 10 can be used for either eye by simply rotating the aid 180° to conform to the contour of the other side of the face. While housing 11 can be made from a variety of materials, injection molded plastics are preferred based on cost, structural rigidity, corrosion resistance and smoothness of surface texture.

An eye drop dispenser seat 14 is provided in housing top 12 and includes a central droplet discharge aperture 15 to permit droplets of opthalmic solution 30 to pass from the dispensing end 31 of medicine dropper 32 to the eye. Dispenser seat 14 is configured to receive and support dispensing end 31 of medicine dispenser 32 a predetermined distance directly above the center of the eye. Thus, in the embodiment shown in FIG. 3, the lower portion of dispenser seat 14 is tapered inwardly to prevent further downward travel of dispenser 32.

A unique feature of the preferred embodiment of application aid 10 is the provision of eye distracting orifice 16 in housing top 12 adjacent to dispenser seat 14. A vexing problem frequently encountered in self-administering eye drops, even when using virtually any of the application aids currently available, is that the eye's attention is focused on the end of the dispenser and the impending droplet of opthalmic solution. All to often, the eye blinks as a reflex action, resulting in the droplet being distributed over the exterior eyelid as opposed to the eye itself. Repeated attempts are often required before success is finally achieved, resulting in frustration and a waste of medicine. Eye distracting orifice 16 solves this problem. Being in view of the eye being treated and permitting light to pass therethrough focuses the eye's attention on the orifice, as shown by the sight line in FIG. 3, instead of on the end of the dispenser and the impending droplet. This virtually eliminates the problem of premature blinking before the droplet has contacted the eye.

Another unique feature of the preferred embodiment is the provision of a vertical alignment indicator in view of the eye being treated which guides the individual in moving his head backward or forward to achieve precise vertical alignment of the eye drop dispenser end before dispensing droplets of the opthalmic solution. This avoids skewed or off center application of the droplets and results in a uniform application of the solution to the surface of the eye.

Figure 4:
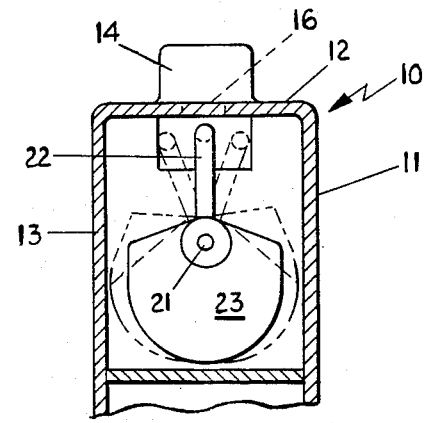
FIG. 4 is an end cross-sectional view of the application aid taken along the line 4—4 of FIG. 3.

In the preferred embodiment shown, the vertical alignment indicator includes an indicator element 20 which is freely rotatably mounted interior of housing 11 parallel to housing side wall 13 on axle pin 21, which is perpendicularly mounted to housing side wall 13. Indicator element 20 includes an indicator point 22 at one end which is perpendicular to the main body of indicator element 20 and extends toward dispenser seat 14 so as to pass by orifice 16 between the eye and orifice 16 during rotation of element 20. The center of gravity of indicator element is located nearer the end opposite the indicator point, below the point of rotatable mounting on axle pin 21. This is accomplished by providing an enlarged portion 23 or by any other means of adding additional weight to that end of the indicator element. Because of this structure, the force of gravity will cause the indicator element to constantly seek a vertical orientation with indicator point 22 on top. Thus, when indicator point 22 is positioned at the center of orifice 16, precise vertical alignment of dispenser 32 is insured, as shown in FIGS. 2-4. FIG. 4 illustrates in phantom the position of indicator needle 22 away from orifice 16 when vertical alignment has not been achieved.

Figure 5:
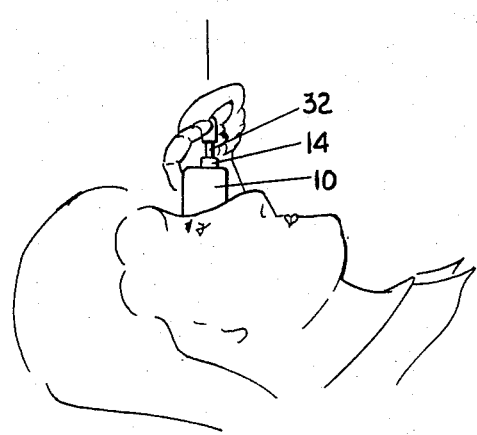
FIGS. 5 and 6 are, respectively, side and front views of an individual self-administering opthalmic solution with the dispenser aid.
Figure 6:
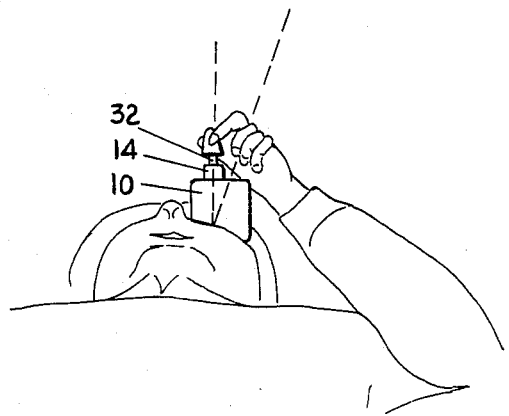

The ease of using application aid 10 is illustrated in FIGS. 5 and 6. Medicine dropper 32, filled with the desired opthalmic solution, is placed in dispenser seat 14. The user's head is then reclined, and application aid 10 is placed over the eye to be treated and oriented until comfortably seated on the facial area around the eye. The eye is then focused on orifice 16, and slight upward or downward movements of the head are made until indicator point 22 is visible centered in orifice 16. With vertical alignment thus insured and with the eye being distracted by orifice 16 and indicator point 22, dispenser 32 is actuated to dispense a droplet of the opthalmic solution onto the surface of the eye.

Figure 7:
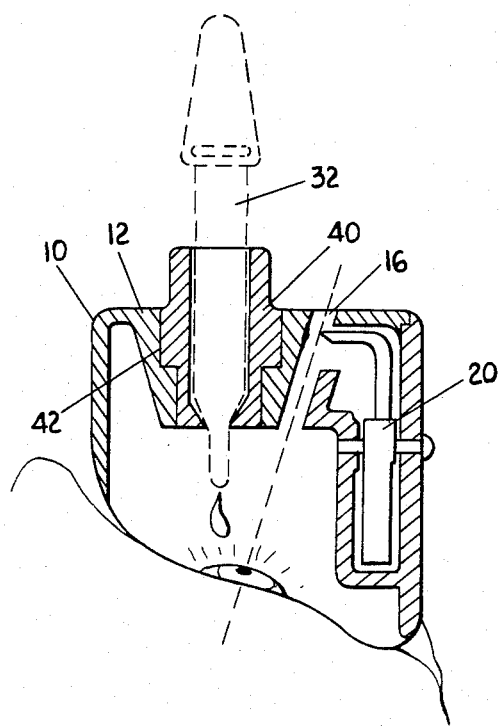
FIGS. 7 and 8 are side cross-sectional elevational views similar to FIG. 3 illustrating alternate embodiments which accommodate dispensers of differing configurations.
Figure 8:
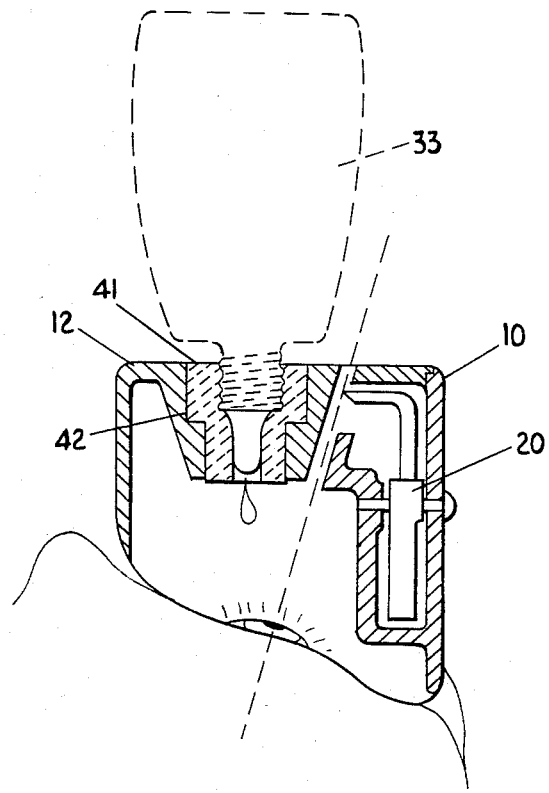

Another unique feature of the application aid of the present invention is shown in FIGS. 7 and 8 in an alternate preferred embodiment. To maximize the versatility of using application aid 10, the dispenser seat can be removably mounted in housing top 12 to permit interchangeability of differently configured dispenser seats to accommodate dispensers of differing configurations. For example, in FIG. 7, a removable dispenser seat element 40 is utilized, which has an internal configuration to accommodate medicine dropper 32 as shown. Because application aid 10 is used in the vertical position shown, a step down diameter dispenser seat receiving aperture 42 and a corresponding mating external step down configuration of insert 40 permits insert 40 to be simply dropped into position where it will remain by the force of gravity.

In FIG. 8, dispenser seat insert 41 is being utilized, which has an internal configuration to accommodate the screw top nozzle end of a plastic squeeze bottle. With the external configuration of insert 41 having the same dimensions and configuration of insert 40, it is quickly and easily interchangeable with insert 40 in aperture 42. Accordingly, the variety of dispensers with which application aid 10 may be used is only limited by the variety of dispenser seat inserts available.

Thus, the present invention provides an eye drop application aid for self-application of droplets of opthalmic solution which is simple in construction and virtually problem-free in use. Precise vertical alignment can be easily and consistently accomplished, insuring accurate and uniform application of the opthalmic solution droplets to the eye. Eye focus distraction eliminates premature blinking, and the dispenser end is captivated at a pre-determined height above the eye, which eliminates any chance of accidental contact and injury to the eye. By a simple change of dispenser seat inserts, the device may be used with a wide variety of configurations of eye drop dispensers.

While the preferred embodiments of the present invention have been described and illustrated, it will be obvious to those skilled in the art that various changes and modifications can be made without departing from the spirit of the present invention. Accordingly, the scope of the present invention is deemed to be limited only by the appended claims.

The embodiments of the present invention in which an exclusive property or privilege is claimed are defined as follows:

1. An eye drop application aid for self-application of droplets of opthalmic solution by an individual comprising:
   a housing having a top, side walls and an open bottom, the lower periphery of said side walls being contoured to conform to the facial area surrounding the eye socket;
   an eye drop dispenser seat in said housing top having a central droplet discharge aperture therethrough for receiving and supporting the dispensing end of an eye drop dispenser a predetermined distance directly above the center of the eye and permitting droplets of opthalmic solution to be applied to the eye; and
   vertical alignment indicator means mounted to said housing adjacent to said dispenser seat in view of the eye being treated whereby said individual can be guided by said indicator to vertically align said eye drop dispenser end by head movement before d',spensing droplets of opthalmic solution to insure accurate application of said droplets to the eye.

2. An eye drop application aid according to claim 1 wherein said vertical alignment indicator means comprises an orifice in said housing top adjacent to said dispenser seat in view of the eye being treated and an indicator element freely rotatably mounted parallel to the housing side wall, said indicator element having an indicator point at one end and a center of gravity nearer the other end below the point of rotatable mounting, said indicator point being positioned to pass by said orifice during rotation of said indicator element, whereby the force of gravity will cause said indicator element to constantly seek a vertical orientation with the indicator point on top, and when said indicator point is positioned at said orifice, said eye drop dispenser end will be vertically aligned above the eye to be treated.

3. An eye drop application aid according to claim 2 wherein said indicator element is freely rotatably mounted interior of said housing on an axle pin which is perpendicularly mounted to said housing side wall and wherein said indicator point is perpendicular to the main body of said indicator element and extends toward said dispenser seat so as to pass by said orifice between the eye and the orifice during rotation.

4. An eye drop application aid according to claim 1 wherein said dispenser seat is removeably mounted in said housing top to permit interchangeability of differently configured dispenser seats to accommodate dispensers of differing configurations.

5. An eye drop application aid kit for self-application of droplets of opthalmic solution by an individual comprising:
   a housing having a top, side walls and an open bottom, the lower periphery of said side walls being contoured to conform to the facial area surrounding the eye socket;
   a dispenser seat receiving aperture positioned in said housing top so as to be above the eye when the device is in a position to dispense eye drops to the eye; and
   a plurality of eye drop dispenser seats interchangeably mountable in said dispenser seat receiving aperture, each dispenser seat having a central droplet discharge aperture therethrough for receiving and supporting the dispensing end of an eye drop dispenser a predetermined distance directly above the center of the eye and permitting droplets of opthalmic solution to be applied to the eye, each dispenser seat being removeably mountable in said housing top to permit interchangeability of differently configured dispenser seats to accommodate dispensers of differing configurations one dispenser seat being shaped to receive a medicine dropper and another dispenser seat having an internally threaded opening that is shaped to receive a screw top of a plastic squeeze bottle.

6. An eye drop application aid for self-application of droplets of ophthalmic soltuion by an individual comprising:
   a housing having a top, side walls and an open bottom, the lower periphery of said side walls being contoured to conform to the facial area surrounding the eye socket;
   an eye drop dispenser seat in said housing top having a central droplet discharge aperture therethrough for receiving and supporting the dispensing end of an eye drop dispenser a predetermined distance directly above the center of the eye and permitting droplets of opthalmic solution to be applied to the eye;
   an eye distracting orifice in said housing top adjacent to said dispenser seat in view of the eye being treated, which permits light to pass therethrough to focus the eye's attention on the orifice, instead of the dispenser end and the impending droplet of opthalmic solution, to avoid premature blinking before the droplet has contacted the eye; and
   vertical alignment indicator means mounted to said housing adjacent to said dispenser seat in view of the eye being treated, whereby said individual can be guided by said indicator to vertically align said eye drop dispenser end by head movement before dispensing droplets of opthalmic solution to insure accurate application of said droplets to the eye.

7. An eye drop application aid according to claim 6 wherein said vertical alignment indicator means comprises an indicator element freely rotatably mounted parallel to the housing side wall, said indicator element having an indicator point at one end and a center of gravity nearer the other end below the point of rotatable mounting, said indicator point being positioned to pass by said orifice during rotation of said indicator element, whereby the force of gravity will cause said indicator element to constantly seek a vertical orientation with the indicator point on top, and when said indicator point is positioned at said orifice, said eye drop dispenser end will be vertically aligned above the eye to be treated.

8. An eye drop application aid according to claim 7 wherein said indicator element is freely rotatably mounted interior of said housing on an axle pin which is perpendicularly mounted to said housing side wall, and wherein said indicator point is perpendicular to the main body of said indicator element and extends toward said dispenser seat so as to pass by said orifice between the eye and the orifice during rotation.

* * * * *